US011399931B2

(12) United States Patent
Woods (10) Patent No.: US 11,399,931 B2
(45) Date of Patent: Aug. 2, 2022

(54) INTRAOCULAR LENS AND METHOD OF CONSTRUCTING THE SAME (71) Applicant: Randall Woods, Sun Lakes, AZ (US)

(72) Inventor: Randall Woods, Sun Lakes, AZ (US)

(*) Notice: Subject to any disclaimer, the term of this patent is extended or adjusted under 35 U.S.C. 154(b) by 196 days.

(21) Appl. No.: 16/532,440

(22) Filed: Aug. 5, 2019

(65) Prior Publication Data
US 2020/0038174 A1 Feb. 6, 2020

Related U.S. Application Data (60) Provisional application No. 62/764,465, filed on Aug. 6, 2018.

(51) Int. Cl.
A61F 2/16 (2006.01)
B29D 11/02 (2006.01)
B29K 83/00 (2006.01)

(52) U.S. Cl.
CPC .......... A61F 2/1635 (2013.01); B29D 11/023 (2013.01); A61F 2002/169 (2015.04); A61F 2240/001 (2013.01); B29K 2083/00 (2013.01); B29K 2995/0046 (2013.01)

(58) Field of Classification Search
CPC .............. A61F 2/1635; A61F 2002/169; A61F 2240/001; B29D 11/023
See application file for complete search history.

(56) References Cited

U.S. PATENT DOCUMENTS

| 4,847,020 A * | 7/1989 | Akhavi .................. A61F 2/161 264/2.2 |
| 9,039,760 B2 | 5/2015 | Brady et al. |
| 2002/0153623 A1* | 10/2002 | Gobron .................. B29C 43/36 264/1.1 |
| 2008/0161914 A1* | 7/2008 | Brady .................. A61F 2/1635 623/6.46 |

* cited by examiner

Primary Examiner — Jerrah Edwards
Assistant Examiner — Christine L Nelson
(74) Attorney, Agent, or Firm — Schmeiser, Olsen & Watts, LLP (57) ABSTRACT An intraocular lens and a method of constructing the intraocular lens are described. The intraocular lens is implanted in a human eye to treat conditions of the eye. The intraocular lens includes a central deformable optic and an annular ring coupled to the deformable optic. The intraocular lens is made by subjecting the deformable optic to compressive forces that reduce the optical power of the deformable optic, and then molding the annular lens to the deformable optic while the deformable optic is undergoing the compressive forces. Once the compressive forces are released, the deformable optic stresses the annular ring along a radial axis of the deformable optic when the intraocular lens is in a natural, unstressed state. The stress or tension between the deformable optic and the annular ring keep the deformable optic from developing deformities that cause visual aberrations.

7 Claims, 9 Drawing Sheets

INTRAOCULAR LENS AND METHOD OF CONSTRUCTING THE SAME

CROSS REFERENCE TO RELATED APPLICATION

This invention claims priority to U.S. provisional patent application Ser. No. 62/764,465, filed Aug. 6, 2018, and entitled "Manufacturing Method for Accommodating Optic", which is incorporated entirely herein by reference.

BACKGROUND OF THE INVENTION

Technical Field

This invention relates to intraocular lenses, and specifically to accommodating intraocular lenses.

State of the Art

An intraocular lens is a man-made lens that is inserted, or implanted, in an eye, often a human eye. The intraocular lens is often implanted in an eye to treat a condition or disease that affects a patient's vision, such as presbyopia or cataracts. Modem intraocular lenses are accommodating intraocular lens, meaning they are capable of changing their focal length and optical power in the eye, providing focusing capability for the patient. A problem with accommodating intraocular lenses is that the lens can form wrinkles or folds as it changes shape in the eye. These wrinkles or folds can distort the image being transmitted through the intraocular lens.

Accordingly, what is needed is an intraocular lens having the ability to change shape through a range of optical power values without distorting the image being transmitted through the intraocular lens.

DETAILED DESCRIPTION OF EMBODIMENTS OF THE INVENTION

As discussed above, the described invention relates to intraocular lenses, and specifically to accommodating intraocular lenses. The disclosed intraocular lens includes a central deformable optic and an annular ring coupled to the deformable optic. A force transfer element is often bonded to the annular ring. The intraocular lens is made by molding the deformable optic and then putting a compressive force on the optic that decreases the optical power of the deformable optic. The annular ring is then bonded onto the circumference of the compressed deformable optic. Once the compressive force on the deformable optic is released, the deformable optic puts a stretching force, also called tension or stresses, on the annular ring when the intraocular lens is in its natural state. The stress forces between the deformable optic and the annular ring keep the deformable optic from getting folds or wrinkles that can cause distortion once the intraocular lens is implanted in the eye.

An intraocular lens is a man-made lens that is implanted in the human eye to treat diseases or other visual issues or conditions of the eye. A human eye can require an intraocular lens implant for various reasons, including cataracts and presbyopia. Any condition of the lens of the human eye which causes an inability of the lens to transmit light or to change optical power, or focal length, may be treated by implanting an intraocular lens into the eye. The intraocular lens can replace the natural lens of the eye. If the natural lens is removed, it is often broken up in the eye and the pieces removed. However, in some, cases the natural lens is left in the eye and the intraocular lens is inserted in the eye in front of the natural lens.

Early intraocular lenses had no accommodating, or focusing, power. These simple intraocular lenses have a single fixed focal length, and, equivocally, a single optical power. The optical power of a lens is a measure of its ability to bend light. A lens with a higher optical power is a stronger lens that bends light more than a lens with a lower optical power. The unit of measure of optical power is the diopter, and optical power is also called diopter power. The optical power of a lens is given by:

$$D_{lens} = 1/f; \quad (1)$$

where $D_{lens}$ is the optical power of the lens in diopters, and f is the focal length of the lens. A lens with a focal length of two meters has an optical power of 0.5 diopters. A lens with a focal length of one-tenth meter has an optical power of 10 diopters. The 10 diopter lens has a greater ability to bend light.

Lenses are formed of one or more optical surfaces that have a change in index of refraction at the surface. A lens surface power, or the optical power of one optical surface of a lens, is given by:

$$D_{surface} = (u-1)/r; \quad (2)$$

where $D_{surface}$ is the lens surface power, u is the index of refraction of the lens material, and r is the radius of curvature of the lens surface. The larger the radius of curvature of a lens surface, the smaller the optical power of that surface, and vice versa.

The optical power of a lens is the addition of the lens surface powers of all of the optical surfaces of the lens. Equation 1 and 2 show the optical power of a lens is determined by the index of refraction of the lens material and the radius of curvature of each of the lens surfaces.

The natural eye lens is a biconvex lens. Most intraocular lenses include a central optic that is a biconvex lens. With a biconvex lens, the smaller the radius of curvature of either surface, the larger the optical power of the lens, and vice versa. The optical power of the natural eye lens is about 23 diopters. However, the natural eye lens has accommodating power, or the ability to change shape and focal length to adjust the focusing power of the eye. This allows the eye to focus on far objects as well as near objects, by accommodating, or changing the optical power of the natural eye lens.

Modern intraocular lenses now provide the ability to accommodate or change optical power and focusing ability of the lens, to allow patients to focus on far or near objects. These are called accommodating intraocular lenses. Intraocular lenses are made to be accommodatable by using deformable material such as molded silicon or other elastic and/or deformable materials that allow the central optic to be deformable and change shape in the eye. Presbyopia is the inability of the natural eye lens to accommodate, and the treatment is often the implantation of an intraocular lens that has accommodating ability to restore the eye back to its original ability to focus on near and far objects. Most accommodating intraocular lenses use the muscles of the eye to accommodate, just as the natural eye lens does. The accommodation range of the eye is the optical power of the eye when focused on a near object minus the optical power of the eye when focused on a far object. The natural eye of a younger person has an accommodation range greater than about 30 diopters. But as humans age, the eye stiffens until the accommodation range approaches zero. Current accommodating intraocular lenses provide about 2-3 diopters of accommodation, which is sufficient for reading at a distance of about 16 inches from the eye. The eye accommodates by putting an accommodation force on the circumference of the natural lens of the eye. In the lens natural state, the lens is at the lower end of the accommodation range, for focusing on far objects. When the eye squeezes on the circumference of the lens, the lens bulges slightly, decreasing the radius of curvature of the front and/or rear surfaces of the lens, and increasing the lens optical power, which provides for near focus of the eye. The accommodating intraocular lens should perform similarly. The intraocular lens central deformable optic should have a desired optical power when the intraocular lens is in an intraocular lens natural state—no forces on the intraocular lens. The desired optical power is chosen to provide the patient with clear far visual focus. When the eye puts a compressive accommodating force around the circumference of the accommodating intraocular lens, the central deformable optic should increase in optical power to provide for clear near visual focus. Similarly, when the eye puts an expanding accommodating force on the accommodating intraocular lens, the central deformable optic should decrease in optical power.

Accommodating intraocular lenses are often made of a molded silicon material, which provides a transparent, flexible intraocular lens. A problem is that when the deformable optic changes shape to accommodate, or change optical power, folds or wrinkles in the deformable optic can occur, which distorts the image transmitted through the intraocular lens. It is desirable to have an accommodating intraocular lens that has a high optical power and a large accommodation range, but a minimum of optical distortion throughout this range. This provides the patient clear vision both far and near.

An accommodating intraocular lens is formed of a deformable central optic and a haptic. The central optic is the portion of the intraocular lens that the patient sees through and must be clear and distortion free. The central optic is often a biconvex lens just like the natural lens of the eye, but this is not meant to be limiting. The central optic can be formed of many different forms and types of optical elements and surfaces. The haptic is the portion of the intraocular lens that engages with the ciliary muscle of the eye to focus the intraocular lens. The haptic can include a force transfer element that engages with the ciliary muscle to transfer accommodating force from the ciliary muscle to the optic.

Figure 1:
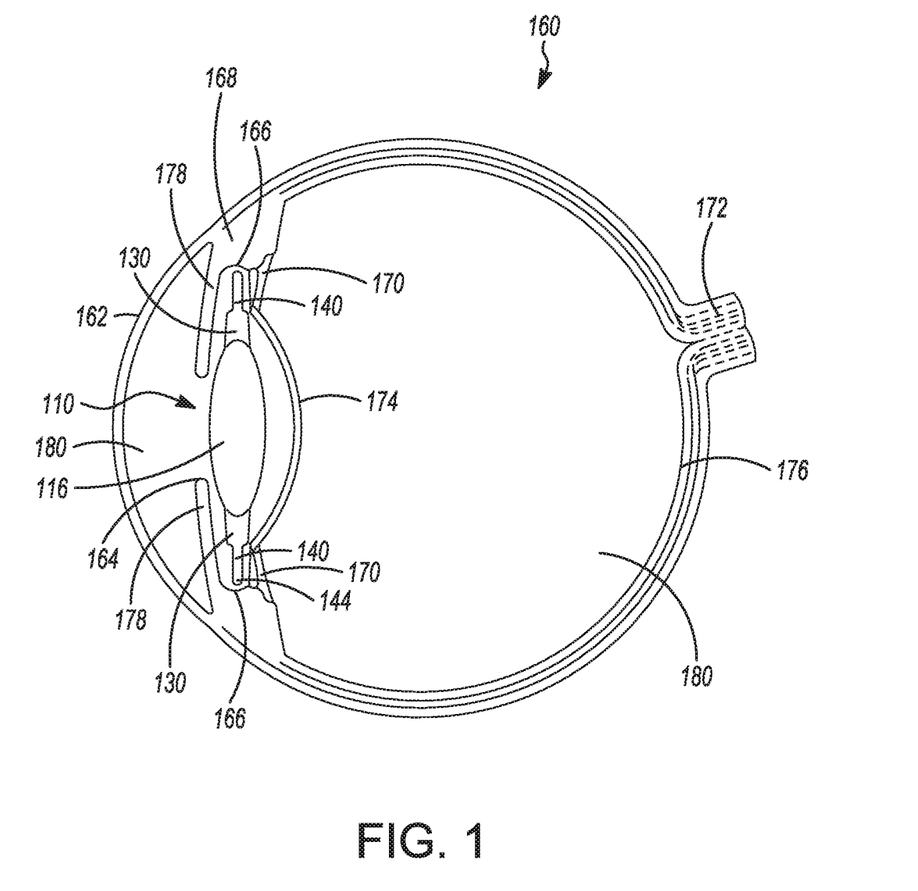
FIG. 1 shows a side view cross-section of an eye with an accommodating intraocular lens implanted in the eye.

Disclosed in an intraocular lens that has an annular ring bonded to the central deformable optic. The haptic of the disclosed intraocular lens includes the annular ring, and, in some embodiments, can also include one or more force transfer elements. The annular ring is molded to the deformable optic when the deformable optic is in a compressed state. Once the annular ring is molded to the deformable optic and the compressive force is released from the deformable optic, the deformable optic wants to return to an uncompressed state, but cannot due to the annular ring bonded about its circumference. In the intraocular lens natural state—there are no outside forces on the intraocular lens or the deformable optic, the optic stresses the annular ring, and vice versa. These stresses, or tension, on the deformable optic, minimize folds, wrinkles, and other deformations of the deformable optic that would cause visual distortions to the patient, FIG. 1 shows a side view cross-section of a human eye 160 having an accommodating intraocular lens 110 implanted into eye 160. Eye 160 includes a cornea 162, an iris 178 that surrounds a pupil 164, a transparent capsular bag posterior portion 174, a ciliary muscle 168 that includes a ciliary sulcus 166 (an indentation in the ciliary muscle 168) and zonules 170 that couple capsular bag posterior portion 174 to ciliary muscle 168. In a natural eye, the capsular bag of the eye includes an anterior portion and a posterior portion, the two sides of the capsular bag. The natural lens is located inside the capsular bag. In eye 160 shown in FIG. 1, the capsular bag anterior portion has been removed, along with the natural lens. Capsular bag posterior portion 174 remans. An aqueous humor 180, a clear optical fluid, fills eye 160 in front of capsular bag posterior portion 174. In the embodiment of eye 160 shown in FIG. 1, intraocular lens 110 is positioned in front of capsular bag posterior portion 174, between capsular bag posterior portion 174 and iris 178. In some embodiments, both the anterior and the posterior portion of the capsular bag are left intact in surgery, and intraocular lens 110 is implanted inside the capsular bag. The outer circumference of intraocular lens 110 is inserted into ciliary sulcus 166 of ciliary muscle 168 so that intraocular lens 110 is easily engaged by ciliary muscle 168. Intraocular lens 110 being engaged by ciliary muscle 168 means that ciliary muscle 168 exerts compressive forces on intraocular lens 110.

The optical image captured by eye 160 is transmitted through cornea 162, passes through pupil 164, is transmitted through intraocular lens 110 and capsular bag posterior portion 174, and is focused onto retina 176. Retina 176 converts the optical image into electrical impulses, which travel down optic nerve 172 to the brain. Ciliary muscle 168 engages intraocular lens 110, exerting accommodating forces on intraocular lens 110 to focus a near or far image onto retina 176.

Figure 2:
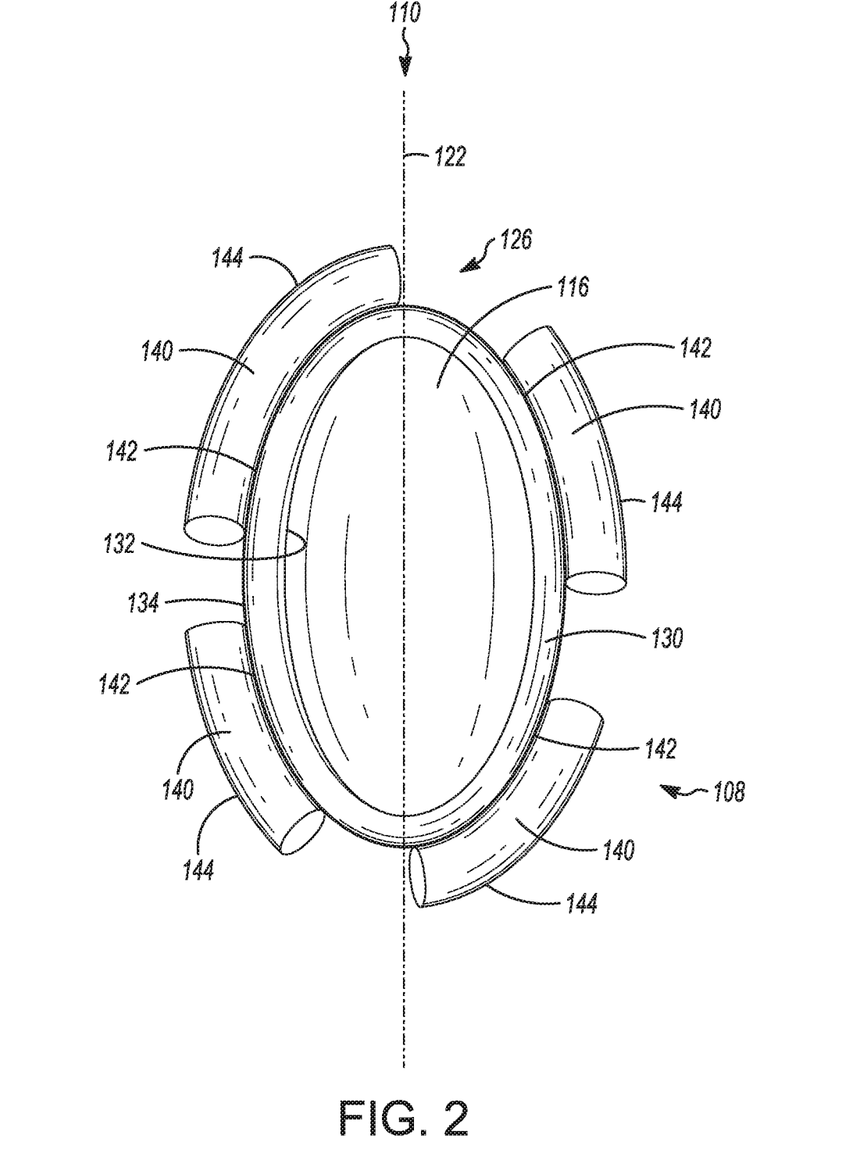
FIG. 2 shows a perspective view of an accommodating intraocular lens.
Figure 3:
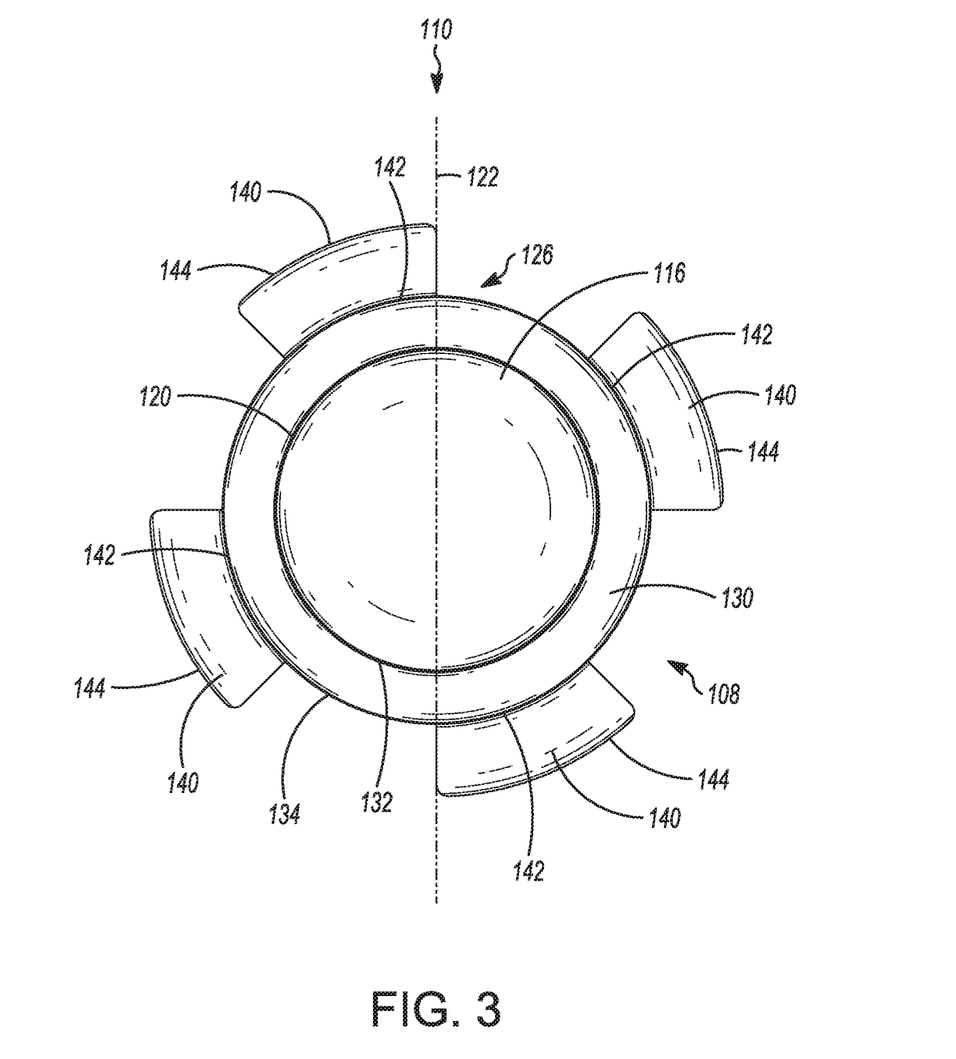
FIG. 3 shows a front view of the intraocular lens of FIG. 2.
Figure 4:
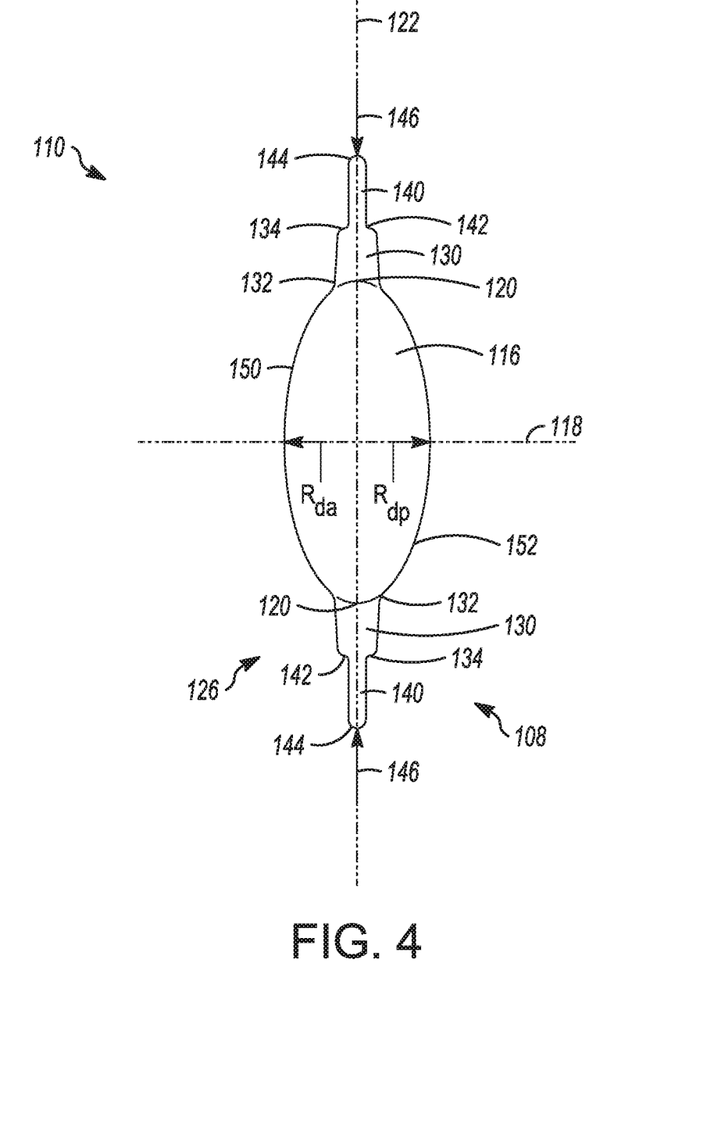
FIG. 4 shows a side view of the intraocular lens of FIG. 2.

FIG. 2 through FIG. 4 shows details of intraocular lens 110. FIG. 2 shows a front perspective view of intraocular lens 110. FIG. 3 shows a front view of intraocular lens 110. FIG. 4 shows a side view of intraocular lens 110. Intraocular lens 110 is formed of flexible, elastic and deformable material, usually silicon. Intraocular lens 110 includes a central deformable optic 116 and a haptic 126. Both deformable optic 116 and haptic 126 are formed of clear moldable silicon, in this embodiment. In this embodiment, haptic 126 includes an annular ring 130 and four force transfer elements 140.

Deformable optic 116 is a biconvex deformable clear silicon lens having a central axis 118, a radial axis 122, and a circumference 120. Central axis 118 extends through the center of deformable optic 116 in the direction of light transmission through deformable optic 116. Radial axis 122 is an axis perpendicular to central axis 118 that extends along a radius of deformable optic 116. Radial axis 122 lies in a circumferential plane of intraocular lens 110, where the circumferential plane is the plane that circumference 120 of deformable optic 116 lies in. Radial axis 122 is perpendicular to central axis 118. Radial axis 122 is only one of many radial axes of deformable optic 116. Each radial axis passes radially through central axis 118 and circumference 120, and are perpendicular to central axis 118. Deformable optic 116 has an anterior surface 150 and a posterior surface 152. Anterior surface 150 and posterior surface 152 change radius of curvature to change the optical power of deformable optic 116 and allow intraocular lens 110 to change focus within its accommodation range. Intraocular lens 110 as shown in FIG. 2 through FIG. 4 is in an intraocular lens natural state 108, meaning no outside forces are on intraocular lens 110. In intraocular lens natural state 108, anterior surface 150 of deformable optic 116 has a desired anterior surface radius of curvature $R_{da}$, as shown in FIG. 4. In intraocular lens natural state 108, posterior surface 152 of deformable optic 116 has a desired posterior surface radius of curvature $R_{dp}$, as shown in FIG. 4. In intraocular lens natural state 108, deformable optic 116 has a desired optical power of deformable optic 116, which is computed by equations 1 and 2 described earlier. This desired optical power of deformable optic 116 is designed to provide the patient with clear vision at the far power end of the accommodating range. The chosen value of the desired optical power depends on the patient's circumstances and whether the natural lens is retained in eye 160 or not. Often the natural lens is not retained in eye 160, as shown in FIG. 1, and the desired optical power of deformable optic 116 is near the natural lens optical power for normal far vision, or resting accommodation, of the natural human eye. It is to be understood, however, that the desired optical power of deformable optic 116 can vary greatly depending on the circumstances of the implantation of intraocular lens 110 and the needs of the patient.

Haptic 126 is the portion of intraocular lens 110 which interacts with eye 160, ciliary muscle 168 in this embodiment, to change the optical power of deformable optic 116. Haptic 126 in the embodiment shown in FIG. 1 through FIG. 4, includes annular ring 130 and force transfer elements 140. In some embodiments, haptic 126 includes only an annular ring, which also acts as the force transfer elements 140. See, for example, FIG. 10 and the accompanying description. In some embodiments, haptic 126 can include elements in addition to annular ring 130 and force transfer elements 140.

Annular ring 130 is a ring of molded clear silicon extending around, and coupled to, circumference 120 of deformable optic 116, see FIG. 2 through FIG. 4. Annular ring 130 is used to keep an amount of tension between deformable optic 116 and annular ring 130 throughout the accommodation range of intraocular lens 110, so that deformable optic 116 does not develop wrinkles, folds, or other distortions as the optical power of deformable optic 116 changes. Annular ring 130, in this embodiment, is formed of the same molded silicon material as optic 126, but this is not meant to be limiting. Annular ring 130 can be formed of many different stretchy or elastic materials that can keep a tension on deformable optic 116. Annular ring 130 has an annular ring inner periphery 132 that is coupled to deformable optic 116. Annular ring 130 has an outer periphery 134 at the outer circumference of annular ring 130, as shown in FIG. 2 through FIG. 5.

Force transfer elements 140 are the elements of intraocular lens 110 that engage ciliary muscle 168 to transfer accommodative forces put on intraocular lens 110 by ciliary muscle 168 to annular ring 130 and deformable optic 116. Haptic 126 of intraocular lens 110 includes at least one force transfer element 140. In the embodiment of intraocular lens 110 shown in FIG. 1 through FIG. 4, intraocular lens 110 has four force transfer elements 140. Each force transfer element 140 is an elongate arc segment that is coupled to, and extends from, outer periphery 134 of annular ring 130, see FIG. 2 through FIG. 4. Each force transfer element 140 is the same design and shape, in the embodiment of intraocular lens 110 shown in FIG. 1 through FIG. 4. Each three transfer element 140 is an arc segment of molded silicon material with an ovoid cross section. Each force transfer element 140 has a three transfer element inner edge 142 that is coupled to—in this embodiment molded to—annular ring outer periphery 134. Each force transfer element 140 has a force transfer element outer edge 144 that engages with ciliary muscle 168 of eye 160. The term "engages" is used here to signify that force transfer element outer edge 144 interacts with ciliary muscle 168, and ciliary muscle 168 puts accommodating forces on force transfer element outer edge 144, which three transfer element 140 transfers to annular ring 130 and deformable optic 116. Force transfer element outer edge 144 is not mechanically coupled to ciliary muscle 168 in this embodiment, but interacts with ciliary muscle 168. Force transfer element 140 deforms deformable optic 116 and annular ring 130 in response to ciliary muscle 168 exerting an accommodating force on force transfer element 140. In some embodiments, force transfer element outer edge 144 can be surgically coupled to ciliary muscle 168, or other elements of eye 160.

It is to be understood that force transfer elements can have many different forms and quantities. In the embodiment of intraocular lens 110 shown in FIG. 1 through FIG. 4, force transfer elements 140 are equally spaced apart from one another along annular ring outer periphery 134, leaving spaces between each force transfer element 140. The spaces between adjacent force transfer elements 140 allows aqueous humor 180 to pass through intraocular lens 110. This circulation of aqueous humor 180 within eye 160 contributes to optimum eye health. In some embodiments, intraocular lens 110 includes only one force transfer element that is a continuous structure along annular ring outer periphery 134. In this example embodiment, when there is only one force transfer element, the force transfer element can have holes or passageways through the force transfer element to allow aqueous humor 180 to pass through. In some embodiments, force transfer elements 140 are not evenly spaced around annular ring outer periphery 134. In some embodiments, force transfer elements 140 take forms other than those shown in the figures. Force transfer elements 140 can have many different shapes and forms and be composed of many different types of material. In some embodiments, intraocular lens 110 includes two force transfer elements 140. In some embodiments, intraocular lens 110 includes seven force transfer elements 140. In some embodiments, intraocular lens 110 includes other numbers of force transfer elements 140. In some embodiments, intraocular lens 110 includes force transfer elements 140 that are not identical is size, shape, and construction. In some embodiments, annular ring 130 serves as the force transfer element, see FIG. 10 and the accompanying description.

Figure 5:
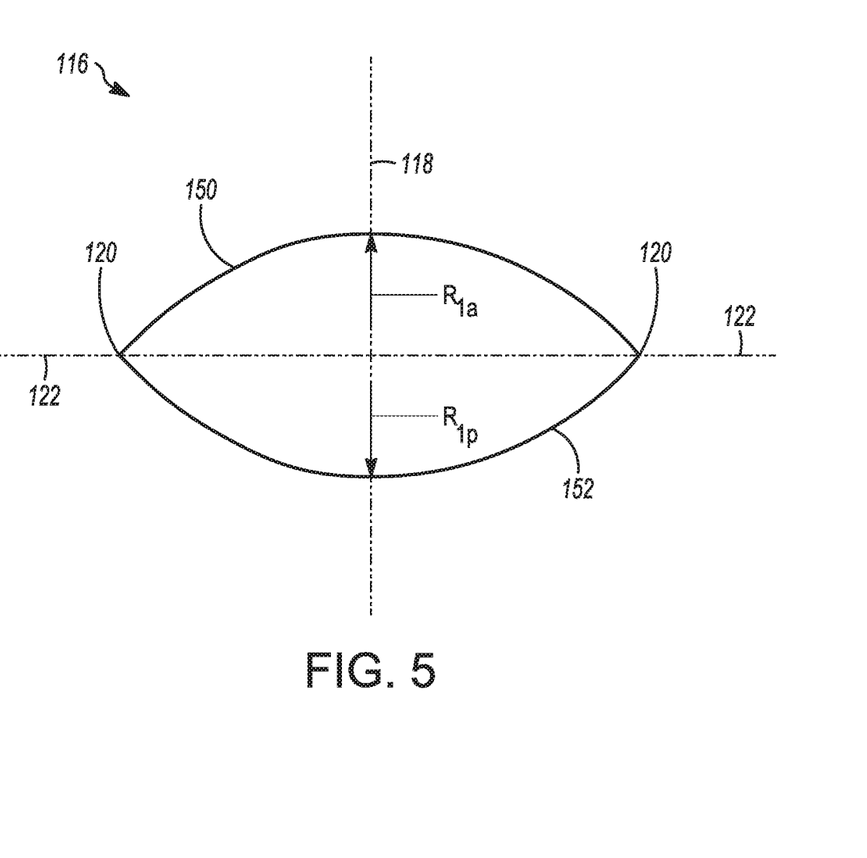
FIG. 5 shows a side cross-section view of a deformable optic.
Figure 6:
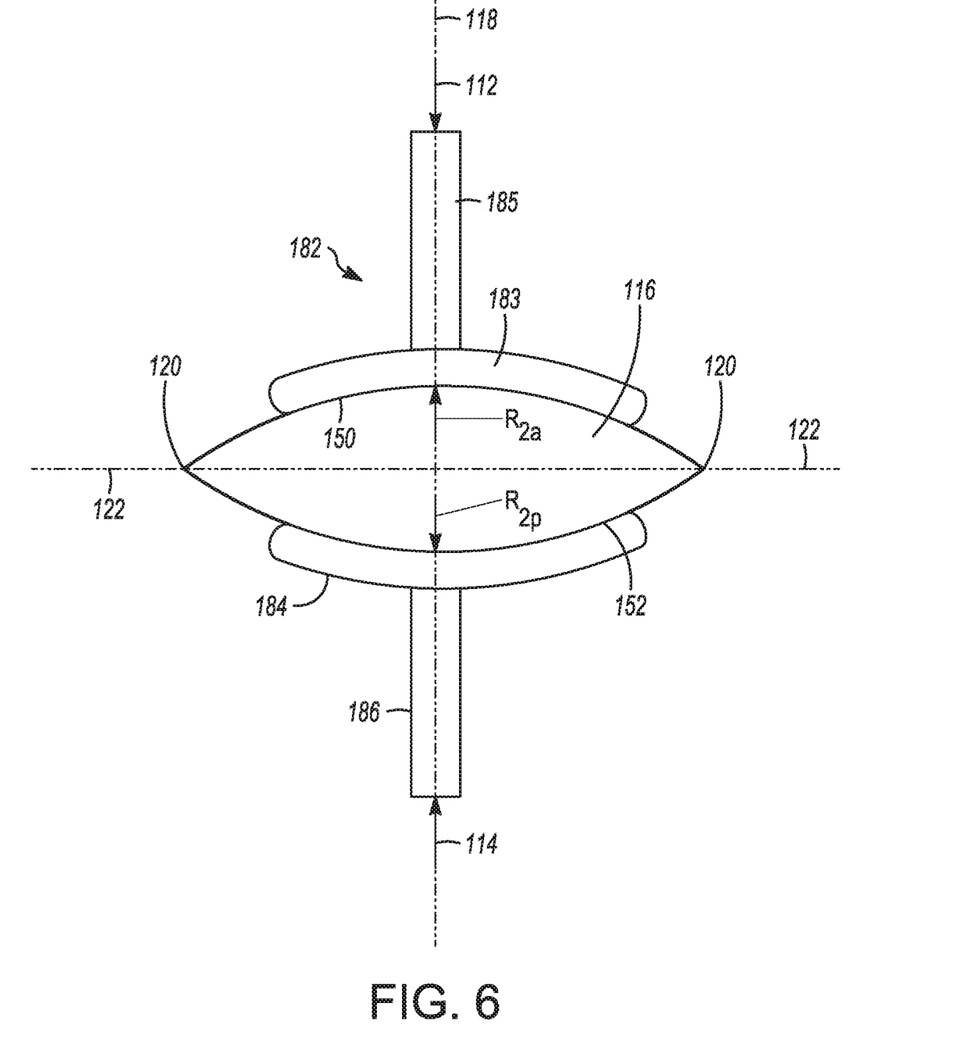
FIG. 6 shows a side cross-section view of the deformable optic of FIG. 5 being compressed.
Figure 7:
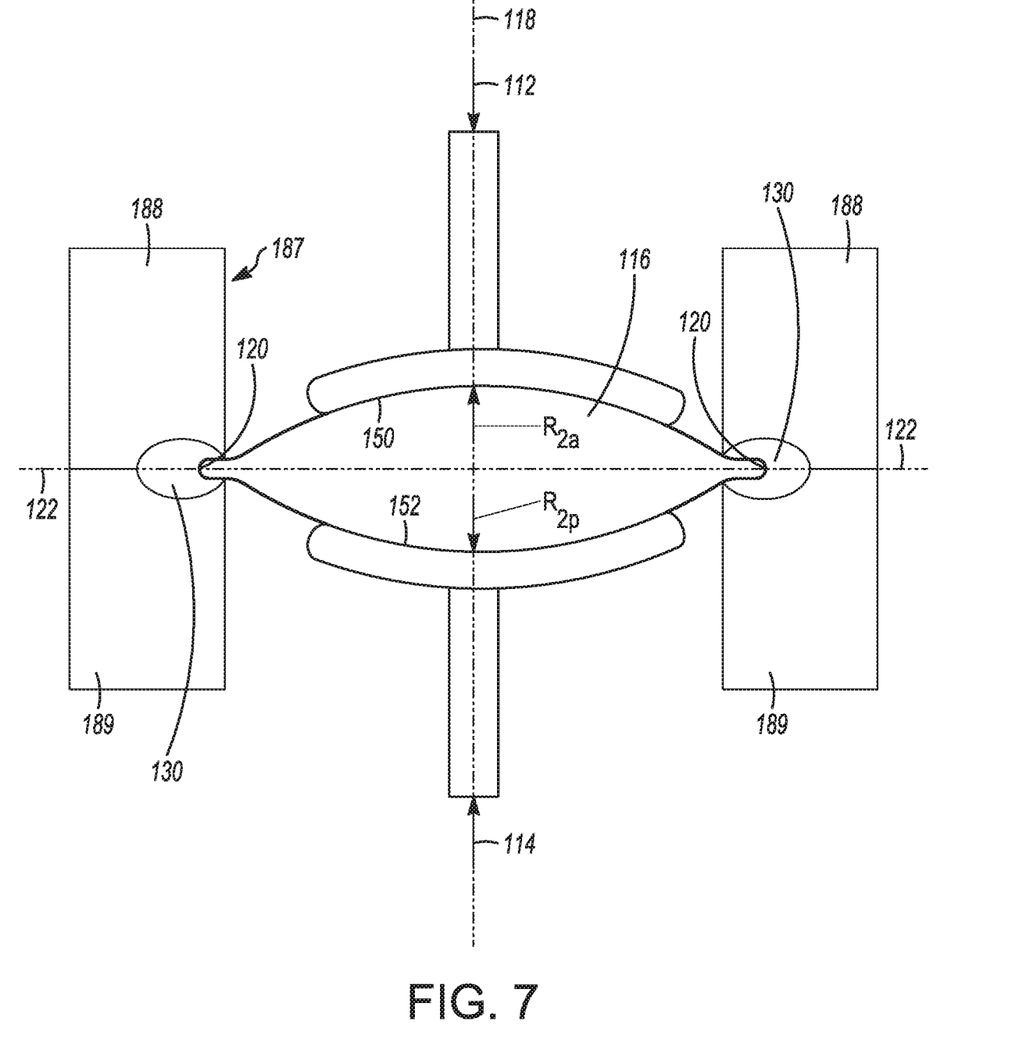
FIG. 7 shows a side cross-section view of an annular ring being molded onto the circumference of the compressed deformable optic of FIG. 6.
Figure 8:
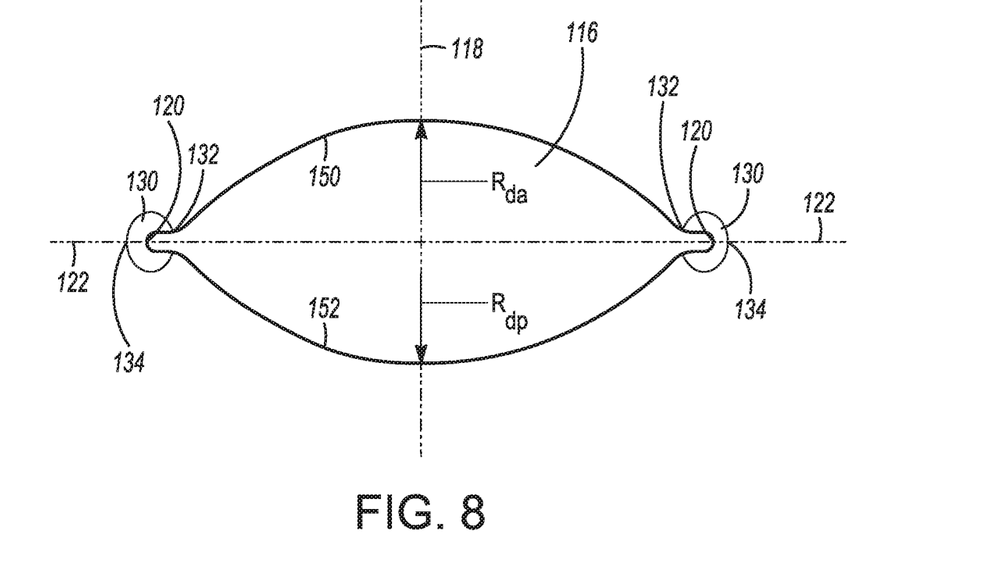
FIG. 8 shows a side cross-section view of the deformable optic with annular ring of FIG. 7 after the mold and the compressive force has been removed.
Figure 9:
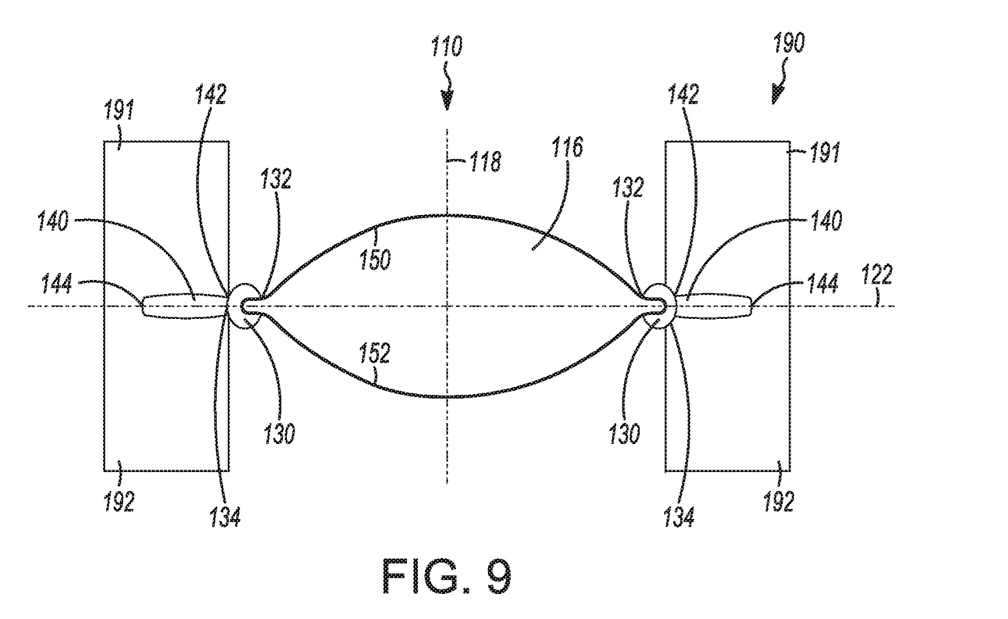
FIG. 9 shows a side cross-section view of force transfer elements being molded to the deformable optic with annular ring of FIG. 8.

FIG. 5 through FIG. 9 illustrate a method of constructing intraocular lens 110. FIG. 5 shows a side view cross-section of deformable optic 116 before annular lens 130 is coupled to deformable optic 116. FIG. 6 shows a side view cross-section of compressive forces being put on deformable optic 116. FIG. 7 shows a side view cross-section of annular ring 130 being molded onto circumference 120 of compressed deformable optic 116. FIG. 8 shows deformable optic 116 and annular ring 130 molded onto deformable optic 116 after annular ring 120 has cured and the compressive forces on deformable optic 116 are removed. FIG. 9 shows force transfer elements 140 being molded onto annular ring 130.

Intraocular lens 110 is constructed in a way that places deformable optic 116 and annular ring 130 in constant tension with each other once intraocular lens 110 is in intraocular lens natural state 108. This constant tension, also called stress or elastic forces, between deformable optic 116 and annular ring 130 keep the surfaces of deformable optic 116 smooth as deformable optic change optical power. The stress and tension between deformable optic 116 and annular lens 120 minimizes folds, wrinkles, and other deformities that can cause visual distortion.

FIG. 5 shows deformable optic 116 after it is formed. "Formed" here means made, constructed, or manufactured. Deformable optic 116 is formed by molding, in this embodiment, and is molded from clear silicon material. Deformable optic 116 is formed to be deformable so that deformable optic 116 can be focused in eye 160. In some embodiments, deformable optic 116 is formed of other materials suitable for an eye lens. In some embodiments, deformable optic 116 is formed by procedures other than molding.

Deformable optic 116 is in a pre-compressed deformable optic natural state as shown in FIG. 5, with no outside forces on deformable optic 116. Deformable optic 116 has a pre-compressed optical power. Anterior surface 150 has a first anterior radius of curvature $R_{1a}$ as shown in FIG. 5. Posterior surface 152 has a first posterior radius of curvature $R_{1p}$. Deformable optic 116 as shown in FIG. 5 has a pre-compressed optical power that is determined by the specific values of first anterior radius of curvature $R_{1a}$, first posterior radius of curvature $R_{1p}$, and the specific index of refraction of the silicon material used for deformable optic 116, as given by equations 1 and 2 discussed earlier. These specific values are chosen based on the visual needs of the patient that intraocular lens 110 is to be inserted into.

FIG. 6 shows deformable optic being compressed by a fixture 182. Fixture 182 puts compressive forces 112 and 114 on deformable optic 116 to decrease the optical power of deformable optic 116. Fixture 182 includes a first pressure plate 183 held by a first arm 185. Fixture 182 also includes a second pressure plate 184 held by a second arm 186. Fixture 182 puts a first compressive force 112 on first arm 185, first pressure plate 183, and deformable optic 116 along central axis 118 of deformable optic 116. Fixture 182 puts a second compressive force 114 on second arm 186, second pressure plate 184, and deformable optic 116 along central axis 118 of deformable optic 116. Fixture 182 has other elements as known in the art to move first and second pressure plates 183 and 184 and first and second arms 185 and 186 to supply the compressive forces 112 and 114, that are not shown for simplicity of the figure. Compressive forces 112 and 114 compress deformable optic 116 and cause a decrease on the optical power of deformable optic 116. Deformable optic 116 is compressed and its optical power reduced prior to molding annular ring 130 around circumference 120 of deformable optic 116 so the once the compressive forces 112 and 114 are released from deformable optic 116, deformable optic 116 tries to return to its deformable optic natural state, and puts stresses and tension on annular ring 130.

It is to be understood that fixture 182 can take many forms to put compressive forces on deformable optic 116 and/or to reduce the optical power of deformable optic 116. In some embodiments, only first or second arm 185 or 186 is moved, with the other being stationary. In some embodiments, only one compressive force 112 or 114 is put on deformable optic 116. In some embodiments, compressive force 112 or 114 is not along central axis 118. Fixture 182 exerts at least one compressive force 112 or 114 on deformable optic 116, where the compressive force 112 or 114 causes a decrease in the optical power of deformable optic 116 from the pre-compressed optical power of deformable optic 116. Fixture 182 can take many forms, as long as it reduces the optical power of deformable optic 116. First pressure plate 183 and second pressure plate 184 are both curved surfaces in the embodiment shown in FIG. 6 and FIG. 7. In some embodiments, first pressure plate 183 and/or second pressure plate 184 is flat instead of curved.

Deformable optic 116 has a compressed optical power after the at least one compressive force is applied. In the embodiment shown in FIG. 6, deformable optic 116 has a compressed optical power after compressive forces 112 and 114 are applied. The compressed optical power is less than both the pre-compressed optical power of deformable optic 116, and a desired optical power of deformable optic 116. The desired optical power is the optical power desired of deformable optic 116 when intraocular lens 110 is in the intraocular lens natural state 108. The value of desired optical power depends on the specifics of the intended use of intraocular lens 110.

The compressed optical power is determined by the radius of curvature of anterior surface 150 and posterior surface 152 when deformable optic 116 is compressed. Anterior surface 150 has a second anterior radius of curvature $R_{2a}$ after compressive forces 112 and 114 are applied to deformable optic 116, as shown in FIG. 6. Posterior surface 152 has a second posterior radius of curvature $R_{2p}$, after compressive forces 112 and 114 are applied to deformable optic 116, as shown in FIG. 6. Deformable optic 116 as shown in FIG. 6 has the compressed optical power that is determined by the specific values of second anterior radius of curvature $R_{2a}$, second posterior radius of curvature $R_{2p}$, and the index of refraction of the silicon material used for deformable optic 116. These specific values are chosen based on the visual needs of the patient that intraocular lens 110 is to be inserted into. The compressed optical power is less than the pre-compressed optical power and the desired optical power of deformable optic 116.

FIG. 7 shows a side view cross-section of annular ring 130 being molded onto compressed deformable optic 116. Once deformable optic 116 is compressed as shown in FIG. 6, annular ring 130 is coupled to deformable optic 116 by molding annular ring 130 to circumference 120 of compressed deformable optic 116. An annular ring mold 187 is used to mold annular ring 130 around circumference 120. Annular ring mold 187, in this embodiment, includes a ring mold upper portion 188 and a ring mold lower portion 189, but this is not meant to be limiting. In this embodiment, ring mold upper portion 188 and ring mold lower portion 189 are each mold rings that clamp onto circumference 120 and form a ring-shaped cavity around circumference 120 that is filled with silicon material and allowed to cure.

It is to be understood that annular ring 130 can be molded or coupled to circumference 120 of deformable optic 116 using many different techniques. Annular ring mold 187 can take many different forms, as is known in mold technology. Annular ring 130 is formed of the same clear silicon material as deformable optic 116 in the embodiment shown in the figures, but this is not meant to be limiting. Annular ring 130 can be formed of many different deformable, stretchy or elastic materials. It is desirable for annular ring 130 to be formed of a stretchy or elastic material so that annular ring 130 can transfer accommodative forces to deformable optic 116, and so that annular ring 130 can keep deformable optic 116 in a state of constant tension or stress once intraocular lens 110 is ready for implantation in eye 160.

FIG. 8 shows a side view cross-section of deformable optic 116 and annular ring 130 after annular ring 130 is molded onto circumference 120, allowed to cure, and annular ring mold 187 is removed. In FIG. 7, compressive forces 112 and 114 have been released. Once compressive forces 112 and 114 are released, deformable optic 116 and annular ring 130 have the shape they have in the intraocular lens natural state 110. Deformable optic 116 tries to return to its pre-compressed state, but cannot because of annular ring 130. Deformable optic 116 stresses, or puts tension on, annular ring 130. Deformable optic 116 stresses, or puts tension on, annular ring 130 along radial axis 122, and along all the radial axes of deformable optic 116, in this embodiment. Annular ring 130 keeps deformable optic 116 from returning to it pre-compressed state. The tension between deformable optic 116 and annular ring 130 keeps deformable optic 116 under stress, which keeps anterior surface 150 and posterior surface 152 from forming folds, wrinkles, or other deformities when deformable optic 116 is in eye 160 and undergoes accommodation.

Deformable optic 116 has the desired optical power after the compressive threes 112 and 114 are released. Anterior surface 150 has a desired anterior radius of curvature $R_{da}$ after compressive forces 112 and 114 are released, when deformable optic 116 is in a post-compressed deformable optic natural state, which is the state the deformable optic 116 is in when intraocular lens 110 is in intraocular lens natural state 108, as shown in FIG. 1 through FIG. 4 and FIG. 8 and FIG. 9. Posterior surface 152 has a desired posterior radius of curvature $R_{dp}$, after compressive forces 112 and 114 are released and deformable optic 116 is in the post-compressed deformable optic natural state. Deformable optic 116 as shown in FIG. 8 has the desired optical power that is determined by the specific values of desired anterior radius of curvature $R_{da}$, desired posterior radius of curvature $R_{dp}$, and the index of refraction of the silicon material used for deformable optic 116. These specific values are chosen based on the visual needs of the patient that intraocular lens 110 is to be inserted into. The desired optical power is less than the pre-compressed optical power but greater than the compressed optical power of deformable optic 116. Releasing the compressive forces 112 and 114 on deformable optic 116 places deformable optic 116 in the post-compressed deformable optic natural state.

Figure 10:
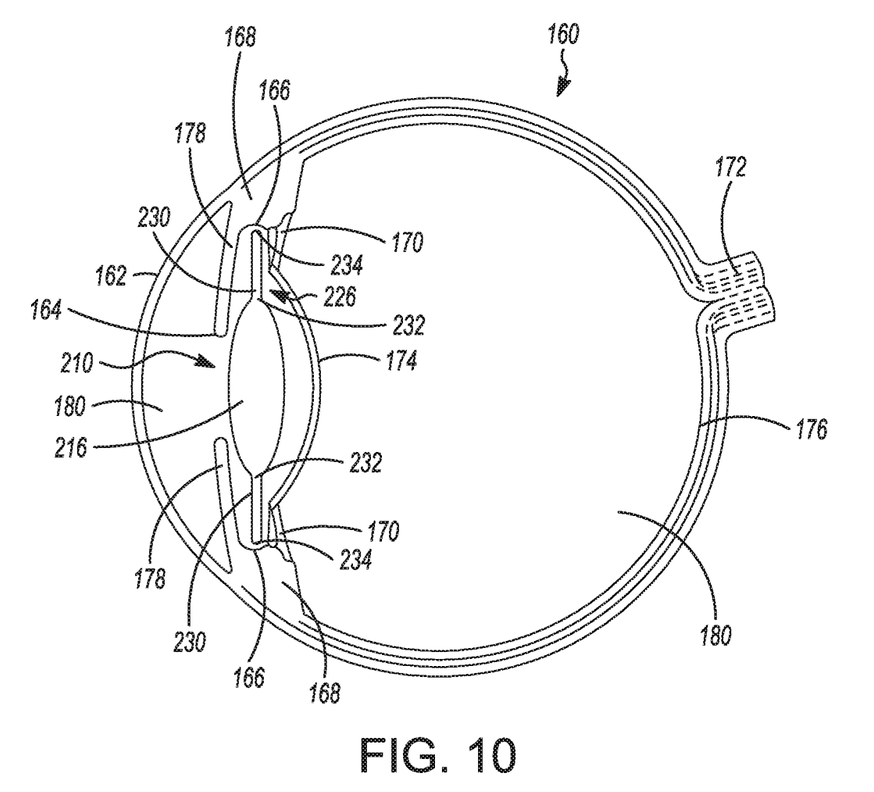
FIG. 10 shows a side view cross-section of an eye with a further embodiment of an accommodating intraocular lens implanted in the eye.

In some embodiments, intraocular lens 110 is complete as shown in FIG. 8, and is ready to be implanted in eye 160, as shown in FIG. 10 and explained in the accompanying description. In the embodiment of intraocular lens 110 shown in FIG. 1 through FIG. 4, intraocular lens 110 still needs force transfer elements 140 coupled to annular ring 130, as shown in FIG. 9.

FIG. 9 shows a side view cross-section of force transfer dements 140 being coupled to annular ring 130 by molding. In this embodiment, a force transfer element mold 190 is used to mold force transfer elements 140 to annular ring 130. Each force transfer element inner edge 142 is molded to annular ring outer periphery 134. Force transfer element mold 190, in this embodiment, has two opposing elements, a force transfer element upper portion 191 and a force transfer element lower portion 192, as shown in FIG. 9. When force transfer element upper portion 191 is mated to force transfer element 192 and to annular ring 130, annular ring outer periphery 134 is adjacent mold openings for each of the four force transfer elements 140. The mold openings are filled with force transfer element material, and allowed to cure, forming each of the four force transfer elements 140 that are coupled to annular ring outer periphery 134, as shown in FIG. 1 through FIG. 4. Once force transfer elements 140 are cured, force transfer element mold 190 is removed, and intraocular lens 110 is complete as shown in FIG. 2 through FIG. 4.

Force transfer elements 140 can be molded from the same material as deformable optic 116 and annular ring 130, or a different material. Force transfer elements 140 need to be rigid enough to transfer accommodating forces from ciliary muscle 168 to annular ring 130 and deformable optic 130. Force transfer element mold 190 can take many forms, as is known in mold technology. In some embodiments, force transfer elements 140 are formed separate from annular ring 130 and then coupled to annular ring 130.

Once force transfer elements 140 are coupled to annular ring outer periphery 134, intraocular lens 110 is complete as shown in FIG. 2 through FIG. 4. Intraocular lens 110 is in intraocular lens natural state 108. Deformable optic 116 is in the deformable optic post-compression natural state, having the desired optical power. Deformable optic 116 stresses annular ring 130 along radial axis 122, and along all the radial axes of deformable optic 116, and along the complete circumference 120 of deformable optic 116. Anterior surface 150 has desired anterior surface radius of curvature $R_{da}$, and posterior surface 152 has desired posterior surface radius of curvature $R_{dp}$.

Once intraocular lens 110 is implanted in eye 160 as shown in FIG. 1, accommodating forces on force transfer elements 140 by eye 160 change the optical power of deformable optic 116, allowing the patient to focus at far and near distances. Deformable optic 116 stresses annular ring 130, along radial axis 122, and along the complete circumference 120 of deformable optic 116, keeping deformable optic 116 free from wrinkles and folds throughout the accommodation range of intraocular lens 110.

FIG. 10 shows a side view cross section of an embodiment of an intraocular lens 210 implanted in eye 160. Intraocular lens 210 is the same as intraocular lens 110 except that intraocular lens 210 does not have force transfer elements that are separate from annular ring 130. Intraocular lens 210 has a haptic 226 that includes annular ring 230 alone, and annular ring 230 as the annular ring and as the force transfer elements for intraocular lens 210. Intraocular lens 210 includes a deformable optic 216 that is the same or similar to deformable optic 116 and has the same description. Intraocular lens 210 has an annular ring 230 coupled to deformable optic using the process described for intraocular lens 110 and shown in FIG. 5 through FIG. 8. Intraocular lens 210 is complete after the molding of annular ring 230 to deformable optic 216, as shown in FIG. 8 for intraocular lens 110. Annular ring 230 is molded to deformable optic 116 in this embodiment. Annular ring 230 includes an annular ring inner periphery 232 that is coupled molded in this embodiment to the circumference of deformable optic 216. Annular ring 230 includes an outer periphery 234 that is engaged by ciliary sulcus 166 of eye 160. Outer periphery 234 of annular ring 230 receives accommodative forces from ciliary muscle 168 and transfers the accommodative forces to annular ring 230 and deformable optic 216 to change the optical power of deformable optic 216 through the accommodation range. Deformable optic 216 is compressed before molding annular lens 230 to deformable optic 216 just like with intraocular lens 110. After annular ring 230 is molded to deformable optic 216 and the compressive forces are released, deformable optic 216 stresses annular ring 230 when intraocular lens 210 is in an intraocular lens natural state as shown in FIG. 10. Deformable optic 216 stresses annular ring 230 along annular ring inner periphery 232 and the circumference of deformable optic 216. Deformable optic 216 stresses annular ring 230 along one or more radial axes of deformable optic 216.

Figure 11:
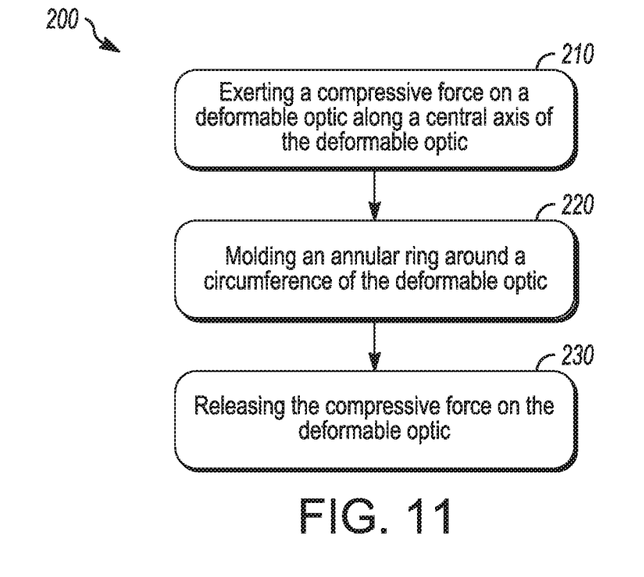
FIG. 11 illustrates a method of constructing an intraocular lens.

FIG. 11 illustrates a method 200 of constructing an intraocular lens. Method 200 includes exerting a compressive force on a deformable optic along a central axis of the deformable optic (210 in FIG. 11). The deformable optic can be formed using many different techniques. In some embodiments, the deformable optic is molded. In some embodiments, the deformable optic is molded of a silicon material. In some embodiments, the deformable optic is molded of an elastic material. The compressive force causes a decrease in an optical power of the deformable optic. The deformable optic has a pre-compressed optical power before the compressive force is applied. The pre-compressed optical power is greater than a desired optical power of the deformable optic. The desired optical power of the deformable optic is the optical power that is desired for the deformable optic once the intraocular lens is completely constructed and the intraocular lens is in an intraocular lens natural state. The intraocular lens natural state is the state intraocular lens is in when it is implanted into the eye, before accommodative forces are applied. The deformable optic has a compressed optical power after the compressive force is applied. The compressed optical power is less than both the pre-compressed optical power and the desired optical power.

In some embodiments more than one compressive force is exerted on the deformable optic, as shown in FIG. 6 and FIG. 7 where two compressive forces are exerted on the deformable optic. In some embodiment the compressive force is not along the central axis of the deformable optic. In some embodiments, at least one compressive force is exerted on the deformable optic, along any axis of the deformable optic, that decreases the optical power of the deformable optic.

Method 200 includes molding an annular ring around a circumference of the compressed deformable optic (220 in FIG. 11). The annular ring is attached to the compressed deformable optic by the molding process, and stays coupled to the deformable optic once the molding is complete. In some embodiments, method 200 includes allowing the annular ring to cure before releasing the compressive force on the deformable optic. In some embodiments, the annular ring is molded of a silicon material. In some embodiments, the annular ring is molded of the same type of silicon material as the deformable optic. In some embodiments, the annular ring is molded of an elastic material.

Method 200 includes releasing the compressive force on the deformable optic, placing the intraocular lens into an intraocular lens natural state (230 in FIG. 11). The deformable optic has the desired optical power after the compressive force is released. Once the compressive force is released, the intraocular lens is in the intraocular lens natural state. The deformable optic stresses, or pulls on, the annular ring when the intraocular lens is in the intraocular lens natural state. The deformable optic stresses, or pulls on, the annular ring because the deformable optic wants to return to its pre-compressed state, but is prevented from doing so by the annular ring. The deformable optic stresses the annular ring along a radial axis of the deformable optic when the intraocular lens is in the intraocular lens natural state. The elastic silicon material of the damnable optic puts tension on the annular ring, and the annular ring elastic material pulls back on the deformable optic. This constant tension between the deformable optic and the annular ring when the intraocular lens is in the intraocular lens natural state keeps the surfaces of the deformable optic smooth. The tension on the deformable optic keeps the deformable optic from developing folds or wrinkles in the deformable optic surfaces, which cause visual distortions to the user of the intraocular lens.

Method 200 can include many other actions. In some embodiments, method 200 includes bonding at least one force transfer element to the annular ring. The force transfer elements transfer accommodative forces exerted on the force transfer element by the eye to the annular ring and the deformable optic.

Disclosed is a method of treating presbyopia of a human eye. The method can be used to treat other conditions of the human eye, such as cataract. The method of treating presbyopia, or other conditions of the human eye, includes implanting an intraocular lens in the human eye. The intraocular lens includes a deformable optic and an annular ring coupled to the deformable optic. The intraocular lens is constructed using method 200 described above, which includes exerting a compressive force on the deformable optic along a central axis of the deformable optic, where the compressive force causes a decrease in an optical power of the deformable optic; molding an annular ring around a circumference of the compressed deformable optic, where the annular ring is coupled to the compressed deformable optic; and releasing the compressive force on the deformable optic. In some embodiments, at least one force transfer element is coupled to the annular ring. The method of treating presbyopia can also include, in some embodiments, engaging the at least one force transfer element with a ciliary muscle of the human eye. In some embodiments, the at least one force transfer element deforms the deformable optic and the annular ring in response to the ciliary muscle exerting an accommodating force on the at least one force transfer element. In some embodiments of the method of treating presbyopia, implanting the intraocular lens in the human eye includes placing the at least one force transfer element into a ciliary sulcus of the ciliary muscle of the human eye.

In some embodiments of the method of treating presbyopia, the intraocular lens is implanted in front of a capsular bag of the human eye.

In some embodiments of the method of treating presbyopia, the deformable optic is molded. The deformable optic can be molded from a silicon material or other elastic, deformable material.

An intraocular lens has been described, and a method of constructing the intraocular lens. The intraocular lens is used to treat conditions of an eye, such as a human eye. The conditions include presbyopia and cataracts. The intraocular lens includes a central deformable optic, which is the element of the intraocular lens that the patient receiving the intraocular lens sees through. The intraocular lens also includes an annular ring that is coupled to, usually molded to, the circumference of the deformable optic. During the manufacturing process, the deformable optic is subjected to compressive forces that reduce the optical power of the deformable optic. The annular lens is molded to the deformable optic while the deformable optic is undergoing the compressive forces. Once the annular ring is coupled to the deformable optic, and the compressive forces are released, the deformable optic stresses the annular ring along an radial axis of the deformable optic when the intraocular lens is in a natural, unstressed state. The opposing stress or tension between the deformable optic and the annular ring in the intraocular lens natural state keeps the deformable optic from developing deformities that cause visual aberrations as the deformable optic is used and focused in the eye. A force transfer element is often coupled to the annular ring to transfer accommodative forces of the eye to the deformable optic.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

The invention claimed is:

1. A method of constructing an intraocular lens, the method comprising:
   providing a formed deformable optic having a pre-compressed optical power;
   exerting a compressive force on the formed deformable optic along a central axis of the formed deformable optic, wherein the compressive force causes a decrease in an optical power of the formed deformable optic from the pre-compressed optical power to a compressed optical power;
   molding an annular ring around a circumference of the compressed formed deformable optic, wherein the annular ring is coupled to the compressed formed deformable optic; and
   releasing the compressive force on the formed deformable optic, placing the intraocular lens into an intraocular lens natural state having a desired optical power, wherein the desired optical power is less than the pre-compressed optical power but greater than the compressed optical power of the formed deformable optic.

2. The method of claim 1, further comprising allowing the annular ring to cure before releasing the compressive force.

3. The method of claim 1, wherein the formed deformable optic stresses the annular ring when the intraocular lens is in the intraocular lens natural state.

4. The method of claim 3, wherein the formed deformable optic stresses the annular ring along a radial axis of the formed deformable optic when the intraocular lens is in the intraocular lens natural state.

5. The method of claim 1, further comprising bonding at least one force transfer element to the annular ring.

6. The method of claim 1, wherein the pre-compressed optical power of the formed deformable optic is greater than a desired optical power of the formed deformable optic.

7. The method of claim 6, wherein the compressed optical power of the formed deformable optic is less than both the pre-compressed optical power and the desired optical power.

* * * * *